(12) United States Patent
Burke

(10) Patent No.: US 6,555,525 B2
(45) Date of Patent: *Apr. 29, 2003

(54) MICROENCAPSULATION AND SUSTAINED RELEASE OF OLIGONUCLEOTIDES

(75) Inventor: Paul A. Burke, Oxnard, CA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 67 days.

This patent is subject to a terminal disclaimer.

(21) Appl. No.: 09/820,587

(22) Filed: Mar. 29, 2001

(65) Prior Publication Data

US 2002/0064557 A1 May 30, 2002

Related U.S. Application Data

(63) Continuation of application No. 09/104,549, filed on Jun. 25, 1998, now Pat. No. 6,265,389, which is a continuation-in-part of application No. 08/934,830, filed on Sep. 22, 1997, which is a continuation of application No. 08/521,744, filed on Aug. 31, 1995, now abandoned.

(51) Int. Cl.[7] ........................ A61K 48/00; A61K 9/14; C07H 21/04
(52) U.S. Cl. ........................ 514/44; 435/6; 435/455; 435/91.1; 536/24.1; 536/24.5; 424/484; 424/486; 424/487; 424/488; 424/489
(58) Field of Search ............... 514/44; 435/6, 435/91.1; 536/455, 24.1, 24.5; 424/484, 486, 487, 488, 489

(56) References Cited

U.S. PATENT DOCUMENTS

| | | | |
|---|---|---|---|
| 4,818,542 A | 4/1989 | DeLuca et al. | 424/491 |
| 4,897,268 A | 1/1990 | Tice et al. | 424/422 |
| 5,019,400 A | 5/1991 | Gombotz et al. | 424/497 |
| 5,126,147 A | 6/1992 | Silvestri et al. | 424/497 |
| 5,478,564 A | 12/1995 | Wantier et al. | 424/426 |
| 5,641,754 A | 6/1997 | Iversen | |
| 5,656,297 A | 8/1997 | Bernstein et al. | |
| 5,656,611 A | 8/1997 | Kabanov et al. | 514/44 |
| 5,693,773 A | 12/1997 | Kandimalla et al. | 536/22.1 |
| 5,756,476 A | 5/1998 | Epstein et al. | |
| 6,087,324 A | 7/2000 | Igari et al. | 514/2 |
| 6,265,389 B1 * | 7/2001 | Burke | 514/44 |

FOREIGN PATENT DOCUMENTS

| | | |
|---|---|---|
| EP | 0251680 A2 | 6/1987 |
| EP | 0266119 A3 | 10/1987 |
| EP | 0330180 A1 | 2/1989 |
| EP | 0537559 A1 | 10/1992 |
| EP | 0633020 A1 | 7/1994 |
| WO | WO 90/09166 | 8/1990 |
| WO | WO 90/13285 A1 | 11/1990 |
| WO | WO 90/13780 | 11/1990 |
| WO | WO 91/12882 A1 | 9/1991 |
| WO | WO 92/11844 | 7/1992 |
| WO | WO 91/12882 | 9/1992 |
| WO | WO 93/01286 A2 | 1/1993 |
| WO | WO 93/02712 A1 | 2/1993 |
| WO | WO 94/15646 | 7/1994 |
| WO | WO 94/23699 A1 | 10/1994 |
| WO | WO 94/23738 A1 | 10/1994 |
| WO | WO 95/11010 | 4/1995 |
| WO | WO 95/29664 A1 | 11/1995 |
| WO | WO 96/07399 A1 | 3/1996 |
| WO | WO 96/40074 | 12/1996 |
| WO | WO 98/08858 A1 | 3/1998 |

OTHER PUBLICATIONS

Costantino, H.R. et al, "Solid–Phase Aggregation of Proteins under Pharmaceutically Relevant Conditions," *Journal of Pharmaceutical Sciences*, 83 (12) : 1662–1669 (1994).

Costantino, H.R. et al., "Moisture–Induced Aggregation of Lyophilized Insulin," *Pharmaceutical Research*, 11 (1) : 21–29 (1994).

Costantino, H.R. et al., "Aggregation of a Lyophilized Pharmaceutical Protein, Recombinant Human Albumin: Effect of Moisture and Stabilization by Excipients," *Biotechnology*, 13:493–496 (1995).

Langer, R., "New Methods of Drug Delivery," *Science*, 249:1527–1533 (Sep. 28, 1990).

Liu, W.R. et al., "Moisture–Induced Aggregation of Lyophilized Proteins in the Solid State," *Biotechnology and Bioengineering*, 37:177–184 (1991).

Lu, W. and Park, T.G., "Protein Release from Poly(lactic-co-glycolic acid) Microspheres: Protein Stability Problems," *PDA Journal of Pharmaceutical Science & Technology*, 49(1):13–19 (Jan.–Feb. 1995).

Watson, P.H. et al., "Inhibition of c–myc Expression by Phosphorothioate Antisense Oligonucleotide Identifies a Critical Role for c–myc in the Growth of Human Breast Cancer," *Cancer Research*, 51: 3996–4000 (Aug. 1, 1995).

Wagner, R.W., "Gene Inhibition Using Antisense Oligodeoxynucleotides," *Nature*, 372: 333–335 (Nov. 24, 1994).

(List continued on next page.)

Primary Examiner—Sean McGarry
(74) Attorney, Agent, or Firm—Hamilton, Brook, Smith & Reynolds, P.C.

(57) ABSTRACT

This invention relates to a composition, and method of forming and using the composition, for the sustained release of oligonucleotides, in particular antisense ODNs. The sustained release composition of this invention comprises a polymer matrix of a biocompatible polymer and stabilized oligonucleotide, wherein the stabilized oligonucleotide is dispersed within the biocompatible polymer.

The method of the invention, for forming a composition for the sustained release of oligonucleotide, in particular an antisense ODN, includes dissolving a polymer in a polymer solvent to form a polymer solution, dispersing stabilized oligonucleotide in the polymer solution, and then solidifying the polymer to form a polymeric matrix containing a dispersion of the stabilized oligonucleotide.

The method of using the sustained release composition of the present invention comprises providing a therapeutically effective blood level of oligonucleotide in a subject for a sustained period by administering to the subject a dose of the sustained release composition described herein.

15 Claims, 2 Drawing Sheets

OTHER PUBLICATIONS

Cohen, J.S., "Oligonucleotides as therapeutic Agents," *Pharmac. Ther.*, 52: 211–225 (1991).

Akhtar, S. and Ivinson, A.J., "Therapies That Make Sense," *Nature Genetics*, 4: 215–217 (Jul., 1993).

Akhtar, S. and Lewis, K.J., "Antisense Oligonucleotide Delivery to Cultured Macrophages is Improved by Incorporation into Sustained–Release Biodegradable Polymer Microspheres," *International Journal of Pharmaceutics*, 151: 57–67 (1997).

Lewis, K.J. et al., "Biogradable Poly (L–lactic acid) Matrices for the Sustained Delivery of Antisense Oligonucleotides," *Journal of Controlled Release*, 37: 173–183 (1995).

Yamakawa, I. et al., "Release Behavior of Poly(Lactic Acid–co–Glyolic Acid) Implants Containing Phosphorothioate Oligdeoxynucleotide," *Biol. Pharm. Bull.* 20 (4) : 455–459 (1997).

Cleek, R. L. et al., "Inhibition of Smooth Muscle Cell Growth in vitro by an Antisense Oligodeoxynucleotide Released from Poly (DL–Lactic–co–Glycolic Acid) Microparticles," *Journal of Biomedical Materials Research*, 35: 525–530 (1997).

Skorski, T. et al., "Leukemia Treatment in Severe Combined Immunodeficiency Mice by Antisense Oligodeoxynucleotides Targeting Cooperating Oncogenes," *J. Exp. Med. 182*: 1645–1653 (Dec. 1995).

Skorski, T. et al., "Antisense Oligodeoxynucleotide Combination Therapy of Primary Chronic Myelogenous Leukemia Blast Crisis in SCID Mice," *Blood* 88:1005–1012 (1996).

Skorski, T. et al., "Suppression of Philadelphia Leukemia Cell Growth in Mice by BCR–ABL Antisense Oligodeoxynucleotide," *Proc. Natl. Acad. Sci. USA 91*: 4505–4508 (May 1994).

Venturelli, D. et al., "Inhibition of T–cell Proliferation by a MYB Antisense Oligomer is Accompanied by Selective Down–Regulation of DNA Polymerase $\alpha$ Expression," *Proc. Natl. Acad. Sci. USA 87*: 5963–5967 (Aug. 1990).

Szczylik, C. et al., "Selective Inhibition of Leukemia Cell Proliferation by BCR–ABL Antisense Oligodeoxynucleotides," *Science 253*: 562–565 (Aug. 2, 1991).

Leonetti, C. et al., "Antitumor Effect of c–myc Antisense Phosphorothioate Oligodeoxynucleotides on Hman Melanoma Cells In Vitro and in Mice," *Journal of the National Cancer Institute*, 88(7) : 419–429 (Apr. 3, 1996).

Crooke, S.T., "Oligonucleotide Therapeutics," *In: Wolff ME (ed) Burger's Medicinal Chemistry and Drug Discovery*, $5^{th}$ Edn. 1. Principles and Practice. Wiley, New York (1995).

\* cited by examiner

SEQUENCE LISTING (1) GENERAL INFORMATION:

(iii) NUMBER OF SEQUENCES: 2

-continued (2) INFORMATION FOR SEQ ID NO: 1:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 1:

AACGTTGAGG GGCAT                                             15

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 2:

CCCTGCTCCC CCCTGGCTCC                                   20

MICROENCAPSULATION AND SUSTAINED RELEASE OF OLIGONUCLEOTIDES

RELATED APPLICATIONS

This application is a Continuation of U.S. patent application Ser. No. 09/104,549, filed Jun. 25, 1998 and now U.S. Pat. No. 6,265,389, which is a Continuation-in-Part of U.S. patent application Ser. No. 08/934,830, filed Sep. 22, 1997, which is a Continuation of U.S. patent application Ser. No. 08/521,744, filed Aug. 31, 1995 and now abandoned. All of the above are incorporated herein by reference in their entirety.

BACKGROUND OF THE INVENTION

Antisense oligonucleotides are modified synthetic oligonucleotides which can inhibit gene expression. For example, antisense oligodeoxynucleotides (ODNs) are modified oligodeoxynucleotides which can inhibit gene expression by interfering with messenger RNA (mRNA) translation. More specifically, many antisense ODNs are designed to bind tightly to mRNA that serves as a template to synthesize a protein. Since the RNA template is known as the "sense" strand, the complementary sequence that binds to it is called the antisense strand. An antisense drug can act, for example, by destroying the targeted mRNA as a result of binding to it, thereby invoking the activity of a ubiquitous cellular enzyme ribonuclease H (RNase H). This enzyme will cleave RNA that is bound to DNA. As such, antisense ODNs are useful, for example, in the treatment of diseases where a particular protein has been identified as critical for a disease to flourish. Many antisense ODNs are modified by replacement of one of the phosphate oxygens in the backbone by a sulfur, so that the antisense ODN is not a poly(phosphodiester) but a poly(phosphorothioate). Antisense ODNs of this type are typically designated [S]ODNs.

Antisense ODNs and other therapeutic oligonucleotides such as, ribozymes, antisense oligoribonucleotides, peptide nucleic acids, decoy RNAs and "dumbbell" DNAs, also known as transcription factor decoy DNAs, are typically administered intravenously. Many conditions which can be treated by oligonucleotide drug therapy require repetitive administration of the oligonucleotide, such as an antisense ODN, which can be problematic with regard to patient compliance.

Therefore, a need exists for a means of delivering oligonucleotides, such as antisense ODNs, which eliminates the need for repetitive administration without inordinately reducing the activity or potency of the ODN released.

SUMMARY OF THE INVENTION

This invention relates to a composition, and method of forming and using said composition, for the sustained release of oligonucleotides, in particular, antisense ODNs. The sustained release composition of this invention comprises a polymeric matrix of a biocompatible polymer and stabilized oligonucleotide, for example, a stabilized antisense ODN, wherein the stabilized oligonucleotide is dispersed within the biocompatible polymer. In a particular embodiment, the oligonucleotide is a stabilized antisense ODN. In a more particular embodiment, the stabilized antisense ODN is in the form of particles.

The method of the invention, for forming a composition for the sustained release of oligonucleotides, includes dissolving a polymer in a polymer solvent to form a polymer solution, dispersing or dissolving the stabilized oligonucleotide, for example, a stabilized antisense ODN in the polymer solution, and then solidifying the polymer to form a polymeric matrix as microparticles containing the stabilized oligonucleotide.

The method of using the sustained release composition of the present invention comprises providing a therapeutically effective blood level of oligonucleotide, such as an antisense ODN, in a subject for a sustained period by administering to the subject a dose of the sustained release composition described herein.

The sustained release composition of the invention overcomes the problem of high initial release of an oligonucleotide in vivo, which is exhibited when the oligonucleotide, in particular an antisense ODN, is not stabilized prior to incorporation into the polymeric matrix. Further, loss of activity of the oligonucleotide, such as an antisense ODN due to instability of the medicament, and chemical interactions between the oligonucleotide and other components contained in or used in formulating the sustained release composition are substantially absent.

The advantages of the sustained release formulation for oligonucleotides, for example, antisense ODNs, as described herein, include increased patient compliance and acceptance by eliminating the need for repetitive administration, increased therapeutic benefit by eliminating fluctuations in oligonucleotide concentration in blood levels by providing a desirable release profile, and a potential lowering of the total amount of the oligonucleotide, in particular an antisense ODN, necessary to provide a therapeutic benefit, by reducing these fluctuations.

DETAILED DESCRIPTION OF THE INVENTION

Figure 1:
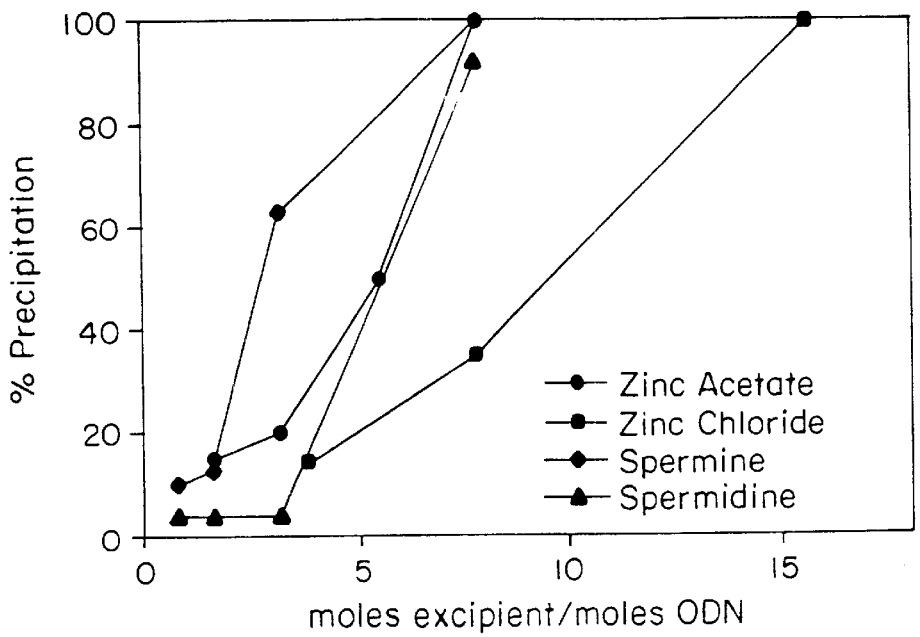
FIG. 1 is a plot of the percent precipitation of antisense ODN versus the molar ratio of excipient to antisense ODN.

Antisense oligodeoxynucleotides (ODNs) are modified synthetic oligodeoxynucleotides which can inhibit gene expression by interfering with messenger RNA (mRNA) translation. Many antisense ODNs are designed to bind tightly to mRNA that serves as a template to synthesize a protein. Since the RNA template is known as the "sense" strand, the complementary sequence that binds to it is called the antisense strand. As such, the ODN can act, for example, by destroying the targeted mRNA as a result of binding to it, thereby invoking the activity of a ubiquitous cellular enzyme ribonuclease H (RNase H). This enzyme will cleave RNA that is bound to DNA.

Antisense ODNs which function through binding to a single-stranded mRNA to form a double helix and thereby control gene expression have been advanced to human clinical trials. See, for example, Agrawal et al., *Antisense*

Res. Dev., 2:261 (1992); Bayever et al., *Antisense Res. Dev.*, 3:383 (1993); Crook et al., *Clin. Pharm. Therap.*, 56:641 (1994); Zhang et al., *Clin. Pharm. Therap.*, 58:44 (1995).

Other antisense ODNs function by the formation of triplexes with target DNA duplexes through Hoogsteen base pairing. Examples of this type of antisense ODN can be found in U.S. Pat. No. 5,693,773, the entire content of which is incorporated herein by reference.

Many antisense ODNs are modified by replacement of one of the phosphate oxygens in the backbone by a sulfur, so that the ODN is not a poly(phosphodiester) but a poly (phosphorothioate). ODNs of this type are typically designated [S]ODNs. Examples, of antisense [S]ODNs include, but are not limited to, a 15-mer antisense [S]ODN having the sequence 5'-AACGTTGAGGGGCAT-3' (SEQ ID NO. 1) complementary to the translation initiation region of c-myc mRNA and a 20-mer antisense [S]ODN having the sequence 5'-CCCTGCTCCCCCCTGGCTCC-3' (SEQ ID NO. 2). Other modifications of antisense ODNs include replacement of the phosphate oxygen in the backbone with an —OR group to give a poly(phosphate triester), with a methyl group to give a poly(methylphosphonate) or with an —NR2 group to give a poly(phosphoramidate). See, Cohen et al., *Pharmac. Ther.* 52:211 (1991), the entire content of which is incorporated herein by reference, which describes modifications of the antisense ODN backbone.

In addition to antisense ODNs, other oligonucleotides which are suitable for use in the invention described herein include, but are not limited to, ribozymes, antisense oligoribonucleotides, peptide nucleic acids, decoy RNAs, and "dumbbell" DNAs also known as transcription factor decoy DNAs.

As defined herein, a sustained release of oligonucleotides, such as an antisense ODN, is release of the oligonucleotide from a biocompatible polymeric matrix which occurs over a period which is longer than that period during which a biologically significant amount of the oligonucleotide, would be available following direct administration of a solution of the oligonucleotide. It is preferred that a sustained release be a release of oligonucleotide which occurs over a period of greater than two days. A sustained release of oligonucleotide, for example an antisense ODN, from a polymeric matrix can be a continuous or a discontinuous release, with relatively constant or varying rates of release. The continuity of release and level of release can be affected by the type of polymer composition used (e.g., monomer ratios, molecular weight, and varying combinations of polymers), oligonucleotide loading, and/or selection of excipients to produce the desired effect.

A "therapeutically effective amount", as used herein, is the amount of the composition for the sustained release of an oligonucleotide from a polymeric matrix, necessary to elicit the desired biological response following administration. "Stabilized oligonucleotide", as that term is used herein, refers to an oligonucleotide which can be stabilized against degradation, loss of potency and/or loss of biological activity, all of which can occur during formation of the sustained release composition, and prior to and during in vivo release. In one embodiment, stabilization can result in a decrease in the solubility of the oligonucleotide, the consequence of which is a reduction in the initial release of oligonucleotide from the sustained release composition in addition to prolongation of the sustained release period. In a preferred embodiment, the stabilized oligonucleotide is a "stabilized antisense ODN."

Stabilization of the oligonucleotide can be accomplished, for example, by the use of a stabilizing agent. "Stabilizing agent", as that term is used herein, is any agent which binds or interacts in a covalent or non-covalent manner with the oligonucleotide, for example an antisense ODN. For example, a metal cation can be complexed with the oligonucleotide, or the oligonucleotide can be complexed with a polycationic complexing agent such as protamine, albumin, spermidine and spermine. Suitable metal cations include any metal cation capable of complexing with the oligonucleotide.

A metal cation-stabilized oligonucleotide, as defined herein, comprises an oligonucleotide and at least one type of metal cation wherein the cation is not significantly oxidizing to oligonucleotide. In a preferred embodiment, the metal cation is multivalent, for example, having a valency of +2 or more. Thus for $M^{+n}$, n is an integer equal to one or more. It is preferred that the $M^{+n}$ be complexed to the oligonucleotide. When the oligonucletide is an antisense ODN the metal cation stabilized antisent ODN is referred to as "$M^{+n}$-stabilized ODN". In microparticles comprising $M^{+n}$-stabilized ODN, the tendency of the ODN to exhibit a high initial release from the microparticle and/or to lose biological activity or potency during hydration in vivo and/or due to the process of forming the sustained release composition or the chemical characteristics of a controlled release composition, is reduced by complexing the ODN with a suitable metal cation prior to encapsulation. The $M^{+n}$-stabilized ODN is subsequently dispersed within a polymeric matrix to form a controlled release composition of this invention. In a preferred embodiment, the $M^{+n}$-stabilized ODN is in the form of particles.

Suitable oligonucleotide stabilizing metal cations include biocompatible metal cations. A metal cation is biocompatible if the cation is non-toxic to the recipient, in the quantities used, and also presents no significant deleterious or untoward effects on the recipient's body, such as an immunological reaction at the injection site.

Examples of suitable oligonucleotide stabilizing metal cations include, but are not limited to, $K^+$, $Zn^{+2}$, $Mg^{+2}$ and $Ca^{+2}$. Suitable oligonucleotide stabilizing metal cations also include cations of transition metals, such as $Cu^{+2}$. In a preferred embodiment, $Zn^{+2}$ is used as an ODN-stabilizing metal cation. The suitability of metal cations for stabilizing antisense ODNs and other oligonucleotides, as described herein, can be determined by one of ordinary skill in the art by performing a variety of stability indicating techniques such as polyacrylamide gel electrophoresis, isoelectric focusing, reverse phase chromatography, and HPLC analysis on particles of metal cation-stabilized ODN and other oligonucleotide particles prior to and following encapsulation and release in vivo.

The "polycationic-stabilized oligonucleotide", as defined herein, comprises an oligonucleotide, for example, an antisense ODN having at least one polycationic complexing agent complexed to the oligonucleotide. Suitable oligonucleotide stabilizing polycationic complexing agents include, but are not limited to, protamine, spermine, spermidine and albumin. The suitability of polycationic complexing agents for stabilizing antisense ODNs and other oligonucleotides, as described herein, can be determined by one of ordinary skill in the art in the manner described above for stabilization with a metal cation. An equal weight ratio of polycationic complexing agent to oligonucleotide, such as an antisense ODN, is suitable.

Polymers suitable to form a polymeric matrix of the controlled release composition of this invention are biocompatible polymers which can be either biodegradable or non-biodegradable polymers or blends or copolymers thereof. A polymer is biocompatible if the polymer and any degradation products of the polymer are non-toxic to the recipient and also possess no significant deleterious or untoward effects on the recipient's body, such as an immunological reaction at the injection site. "Biodegradable", as defined herein, means the composition will degrade or erode in vivo to form smaller chemical species. Degradation can result, for example, by enzymatic, chemical and physical processes. Suitable biocompatible, biodegradable polymers include, for example, poly(lactides), poly(glycolides), poly(lactide-co-glycolides), poly(lactic acid)s, poly(glycolic acid)s, polycarbonates, polyesteramides, polyanydrides, poly(amino acids), polyorthoesters, poly(dioxanone)s, poly(alkylene alkylate)s, copolymers or polyethylene glycol and polyorthoester, biodegradable polyurethane, blends, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl flouride, poly(vinyl imidazole), chlorosulphonate polyolefins, polyethylene oxide, blends, and copolymers thereof.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is of about 2,000 Daltons to about 2,000,000 Daltons. In a preferred embodiment, the polymer is biodegradable polymer or copolymer. In a more preferred embodiment, the polymer is a poly(lactide-co-glycolide)(hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 5,000 Daltons to about 42,000 Daltons.

The amount of stabilized oligonucleotide, for example, stabilized antisense ODN, which is contained within the polymeric matrix of a controlled release composition, is a therapeutically or prophylactically effective amount which can be determined by a person of ordinary skill in the art, taking into consideration factors such as body weight, condition to be treated, type of polymer used, and release rate from the polymer.

In one embodiment, an antisense ODN sustained release composition comprises from about 0.01% (w/w) to approximately 50% (w/w) antisense ODN of the dry weight of the composition based on the weight the antisense ODN prior to stabilization. The amount of antisense ODN used will vary depending upon the desired effect of the antisense ODN, the planned release levels, and the time span over which the ODN will be released. A preferred range of antisense ODN loading is between about 0.1% (w/w) to about 30% (w/w) antisense ODN. A more preferred range of antisense ODN loading is between about 0.5% (w/w) to about 15% (w/w) ODN. It is to be understood that these loadings apply to other oligonucleotides suitable for use in the invention, as earlier described.

In another embodiment, an oligonucleotide sustained release composition can contain other excipients. These excipients are added to maintain the potency of the oligonucleotide over the duration of oligonucleotide release. Suitable excipients include, for example, carbohydrates, amino acids, fatty acids, surfactants, and bulking agents, and are known to those skilled in the art. The amount of excipient used is based on ratio to the oligonucleotide, on a weight basis. For amino acids, fatty acids and carbohydrates, such as sucrose, lactose, mannitol, dextran and heparin, the molar ratio of carbohydrate to oligonucleotide, such as an antisense ODN, is typically between about 1:10 and about 20:1. For surfactants, such as Tween™ and Pluronic™, the molar ratio of surfactant to oligonucleotide, such as an antisense ODN, is typically between about 1:1000 and about 1:20.

Bulking agents typically comprise inert materials. Suitable bulking agents are known to those skilled in the art.

The excipient can also be a metal cation component which is separately dispersed within the polymeric matrix. This metal cation component acts to modulate the release of the oligonucleotide and is not complexed with the oligonucleotide. When the stabilized oligonucleotide is a metal cation-stabilized oligonucleotide, the metal cation component which is separately dispersed is referred to as the second metal cation component. The second metal cation component can optionally contain the same species of metal cation, as is contained in the metal cation stabilized oligonucleotide, and/or can contain one or more different species of metal cation. The metal cation component acts to modulate the release of the oligonucleotide, for example, an antisense ODN, from the polymeric matrix of the controlled release composition and can enhance the stability of the oligonucleotide in the composition. A metal cation component used in modulating release typically comprises at least one type of multivalent metal cation. Examples of metal cation components suitable to modulate oligonucleotide, in particular antisense ODN, release include or contain, for example, $Mg(OH)_2$, $MgCO_3$ (such as $4MgCO_3 \cdot Mg(OH)_2 \cdot 5H_2O$, $MgSO_4$, $Zn(OAc)_2$), $ZnSO_4$, $ZnCl_2$, $MgCl_2$ and $Mg_3(C_6H_5O_7)_2$. A suitable ratio of metal cation component to polymer is between about 1:99 to about 1:2 by weight. The optimum ratio depends upon the polymer and the metal cation component utilized. A polymeric matrix containing a dispersed metal cation component to modulate the release of a biologically active agent from the polymeric matrix is further described in U.S. Pat. No. 5,656,297 and co-pending U.S. patent application Ser. No. 08/727,531, the teachings of both of which are incorporated herein by reference in their entirety.

In yet another embodiment, at least one pore forming agent, such as a water soluble salt, sugar or amino acid, is included in the microparticle to modify the microstructure of the microparticle. The proportion of pore forming agent added to the polymer solution is between about 1% (w/w) to about 30% (w/w). It is preferred that at least one pore forming agent be included in a nonbiodegradable polymeric matrix of the present invention. The oligonucleotide sustained release composition of this invention can be formed into many shapes such as a film, a pellet, a cylinder, a disc or a microparticle. A microparticle, as defined herein, comprises a polymeric component having a diameter of less than about one millimeter and having stabilized oligonucleotide dispersed therein. A microparticle can have a spherical, non-spherical or irregular shape. Typically, the microparticle will be of a size suitable for injection. A preferred size range for microparticles is from about one to about 180 microns in diameter.

In the method of this invention for forming a composition for the sustained release of an oligonucleotide, for example, an antisense ODN, a suitable amount of particles of stabilized oligonucleotide is dispersed in a polymer solution.

A suitable polymer solution contains between about 1% (w/v) and about 30% (w/v) of a suitable biocompatible polymer, wherein the biocompatible polymer is typically dissolved in a suitable polymer solvent. Preferably, a polymer solution contains about 2% (w/v) to about 20% (w/v) polymer.

A suitable polymer solvent, as defined herein, is a solvent in which the polymer is soluble, in which some, none, or all of the stabilized oligonucleotide particles are soluble and in which the stabilized oligonucleotide particles are non-reactive. Examples of suitable polymer solvents include polar organic liquids, such as methylene chloride, chloroform, ethyl acetate, methyl acetate, hexafluoroisopropanol, acetone, dimethylsulfoxide and combinations thereof.

To prepare stabilized oligonucleotide particles, such as stabilized antisense ODN particles, the oligonucleotide is mixed in an aqueous solvent, such as water or buffer, with, for example, at least one suitable stabilizing agent such as a metal cation component, or a polycationic complexing agent. In one embodiment, the use of equal weight amounts of the oligonucleotide, for example, an antisense ODN, and stabilizing agent is suitable. In addition, when the stabilization of the oligonucleotide causes a precipitate or suspension, the amount of stabilizing agent used can be the amount necessary to precipitate the desired amount of stabilized oligonucleotide, for example, a stabilized antisense ODN from the aqueous mixture of oligonucleotide and stabilizing agent. This amount can be based on a ratio of moles of stabilizing agent to moles of oligonucleotide, as set forth, for example, in FIG. 1 and Example 2 for antisense ODN. For example, FIG. 1 shows the percent precipitation of an antisense ODN in a 10 mM solution of ODN as a function of the ratio of moles of stabilizing agent to moles of ODN. When a solid is present following stabilization, it is separated from the supernatant using conventional means.

In a preferred embodiment, the oligonucleotide is an antisense ODN which is complexed to a metal cation component, as described herein. In an even more preferred embodiment, the antisense ODN is complexed with $Zn^{+2}$. Complexation is accomplished by mixing, for example, an aqueous solution of the desired antisense ODN with an aqueous solution of the desired metal cation component. Equal weight amounts of the antisense ODN and metal cation component can be employed. In addition, a titration curve for a particular antisense ODN can be generated to determine the ratio of moles of stabilizing agent to moles of antisense ODN needed to precipitate the desired amount of ODN from solution.

Suitable solvents are those in which the antisense ODN and the metal cation component are each at least slightly soluble, such as in water or buffer. For aqueous solvents, it is preferred that water used be either deionized water or water-for-injection (WFI).

It is understood that the oligonucleotide can be in a solid or a dissolved state, prior to being contacted with the metal cation component or polycationic complexing agent. It is also understood that the metal cation component or polycationic complexing agent can be in a solid or a dissolved state, prior to being contacted with the oligonucleotide. In a preferred embodiment, an aqueous solution of oligonucleotide is mixed with an equal weight amount of the metal cation component or polycationic complexing agent which is also in solution.

Typically, the complexed oligonucleotide will be in the form of a precipitate, which is suspended in the solvent. However, the complexed oligonucleotide can also be in solution. In an even more preferred embodiment, the oligonucleotide is complexed with $Zn^{+2}$. The complexed oligonucleotide can then be dried, such as by lyophilization, to form particles of stabilized oligonucleotide, for example antisense ODN. The complexed antisense ODN or other oligonucleotide, which is suspended or in solution, can be bulk lyophilized or can be divided into smaller volumes which are then lyophilized. In a preferred embodiment, the complexed antisense ODN or other oligonucleotide suspension is micronized, such as by use of an ultrasonic nozzle, and then lyophilized to form stabilized oligonucleotide particles. Acceptable means to lyophilize the complexed oligonucleotide mixture include those known in the art.

Preferably, particles of stabilized oligonucleotide, for example, antisense ODN are between about 0.1 to about 10 micrometers or less in diameter. The antisense ODN and other oligonucleotide particles can be fragmented separately, as described in co-pending U.S. patent application Ser. No. 08/006,682, filed Jan. 21, 1993, which describes a process for producing small particles of biologically active agents, which is incorporated herein in its entirety by reference. Alternately, the antisense ODN or other oligonucleotide particles can be fragmented after being added to a polymer solution, such as by means of an ultrasonic probe, homogenization, mechanical shear, or ultrasonic nozzle.

In another embodiment, a metal cation component (also referred to as a second metal cation component when the antisense ODN or other oligonucleotide is stabilized with a metal cation), which is not contained in the metal cation-stabilized antisense ODN or other oligonucleotide particles, is also dispersed within the polymer solution.

It is understood that a metal cation component and the stabilized antisense ODN or other stabilized oligonucleotide can be dispersed into a polymer solution sequentially, in reverse order, intermittently, separately or through concurrent additions. Alternately, a polymer, a second metal cation component and stabilized antisense ODN or other oligonucleotide can be mixed into a polymer solvent sequentially, in reverse order, intermittently, separately or through concurrent additions.

The method for forming a composition for modulating the release of a biologically active agent from a biodegradable polymer is further described in U.S. Pat. No. 5,656,297.

One suitable method for forming oligonucleotide sustained release microparticles from a polymer solution is described in U.S. Pat. No. 5,019,400, issued to Gombotz et al., and co-pending U.S. patent application Ser. No. 08/443,726, filed May 18, 1995, the teachings of which are incorporated herein by reference in their entirety. This method of microparticle formation, as compared with other methods such as phase separation, can also reduce the amount of oligonucleotide, such as an antisense ODN, required to produce a sustained release composition with a specific antisense ODN content.

In this method, a polymer solution, containing the stabilized antisense ODN or other stabilized oligonucleotide which can be present in solution or as a particle dispersion, is processed to create droplets, wherein at least a significant portion of the droplets contains polymer, polymer solvent and the stabilized antisense ODN or other oligonucleotide particles. These droplets are then frozen by means suitable to form microparticles. Examples of means for processing the mixture comprising a polymer solution and the stabilized antisense ODN or other oligonucleotide to form droplets include directing the dispersion through an ultrasonic nozzle, pressure nozzle, Rayleigh jet, or by other known means for creating droplets from a solution.

Means suitable for freezing droplets to form microparticles include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, ethanol mixed with hexane, pentane or oil.

The solvent in the frozen microdroplets is extracted as a solid and/or liquid into the non-solvent to form stabilized antisense ODN or other oligonucleotide containing microparticles. Mixing ethanol with other non-solvents, such as hexane or pentane, can increase the rate of solvent extraction, above that achieved by ethanol alone, from certain polymers, such as poly(lactide-co-glycolide) polymers.

A wide range of sizes of oligonucleotide sustained release microparticles can be made by varying the droplet size, for example, by changing the ultrasonic nozzle diameter. If very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

Yet another method of forming an oligonucleotide sustained release composition, from a polymer solution, includes film casting, such as in a mold, to form a film or a shape. For instance, after putting the polymer solution containing a dispersion of stabilized oligonucleotide particles into a mold, the polymer solvent is then removed by means known in the art, or the temperature of the polymer solution is reduced, until a film or shape, with a consistent dry weight, is obtained. Film casting of a polymer solution, containing a biologically active agent, is further described in U.S. Pat. No. 5,656,297, the teachings of which are incorporated herein by reference in their entirety.

Without being bound by a particular theory it is believed that the release of the oligonucleotide, for example, an antisense ODN, can occur by two different mechanisms. First, the oligonucleotide can be released by diffusion through aqueous filled channels generated in the polymeric matrix, such as by the dissolution of the oligonucleotide, or by voids created by the removal of the polymer solvent during the preparation of the sustained release composition. A second mechanism is the release of oligonucleotide, for example, an antisense ODN due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer. Hydrophilic excipients such as salts, carbohydrates, and surfactants can also be incorporated to increase hydration which can alter the rate of erosion of the polymer.

By altering the properties of the polymer, the contributions of diffusion and/or polymer degradation to oligonucleotide, release can be controlled. For example, increasing the glycolide content of a poly(lactide-co-glycolide) polymer and decreasing the molecular weight of the polymer can enhance the hydrolysis of the polymer and thus, provides an increased oligonucleotide, for example, antisense ODN release from polymer erosion.

In addition, the rate of polymer hydrolysis is increased in non-neutral pH. Therefore, an acidic or a basic excipient can be added to the polymer solution, used to form the microparticle, to alter the polymer erosion rate.

The composition of this invention can be administered to a human, or other animal, by injection, implantation (e.g., subcutaneously, intramuscularly, intraperitoneally, intracranially, and intradermally), administration to mucosal membranes (e.g., intranasally, intravaginally or by means of a suppository), or in situ delivery (e.g., by enema or aerosol spray) to provide the desired dosage of ODN based on the known parameters for treatment with ODN of the various medical conditions.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and scope of the invention be embraced by the defined claims.

The invention will now be further and specifically described by the following examples.

Exemplifications

Polymer

The polymer employed in the following examples was purchased from Boehringer Ingelheim Chemicals, Inc. The polymer is a 10K MW, 50:50 Poly(D,L-lactide-co-glycolide)(PLGA) with hydrophilic end groups referred to as RG 502H.

Process for Preparing Microparticles

Formation of a polymer solution by dissolving polymer in a suitable polymer solvent.

Addition of the stabilized antisense ODN to the polymer solution to form a polymer/antisense ODN mixture. The antisense ODN can be soluble or insoluble in the polymer solution.

Optional homogenization of the polymer/antisense ODN mixture.

Atomization of the polymer/antisense ODN mixture by sonication, and freezing of the droplets by contact with liquid nitrogen.

Extraction of the solvent from the polymer/antisense ODN droplets into an extraction solvent (e.g., −80° C. ethanol), thereby forming particles comprising a polymer/antisense ODN matrix.

Isolation of the particles from the extraction solvent by filtration.

Removal of remaining solvent by evaporation.

Sizing of particles by passage through an appropriately sized mesh so as to produce an injectable product.

EXAMPLE 1

Encapsulation of ODN

An anti-p53 phosphorothioated 20 mer ODN having the sequence 5'-CCCTGCTCCCCCCTGGCTCC-3' (SEQ ID NO. 2) was employed in this Example. Microparticles (Lot A) were prepared by suspending the lyophilized ODN into polymer solution (10% RG 502H in methylene chloride, 5% theoretical load). Additional microparticles (Lot B) were also prepared by co-dissolving the ODN and polymer into DMSO (10% RG 502H in DMSO, 10% theoretical load). In each case, microparticles were prepared using the process described above.

The initial release of the ODN was measured in vitro by incubating approximately 10 mgs of microparticle in 1 ml of 2 mM Tris-Cl, pH 7.8, and measuring the amount released into solution after 24 hours by absorbance at 260 nM. The results are shown in Table 1.

TABLE 1

| Microparticle Lot | Load (Theoretical) | Release at 24 hr. |
|---|---|---|
| A | 5% | 83.8 ± 4.4 |
| B | 10% | 96.7 ± 1.6 |

These results indicated that antisense ODN which is not stabilized prior to encapsulation is released at undesirably high levels within the first 24 hours.

EXAMPLE 2

Precipitation of ODNs with Excipients

A titration curve was generated with spermine, spermidine, zinc acetate, and zinc chloride, in order to assess the ability of these excipients to precipitate an ODN from an aqueous solution. The ODN concentration was fixed at 10 mM and the excipient concentration was varied. The solutions were centrifuged (between 5–15K x g for 5 minutes) and the $OD_{260}$ of the supernatant was measured. From this, the percent precipitation was calculated (from the loss of OD relative to a negative control). The percent of the nucleotide present in the precipitate as a function of the molar ratio of excipient/ODN is plotted in FIG. 1.

EXAMPLE 3

Encapsulation of Complexed ODN

To determine the effect of the complexation on the initial release rate of the antisense ODN of Example 1 from the microparticles, a complex was formed (using either zinc acetate or spermine) and encapsulated using the process described in Examples 1 and 2. To prepare the ODN for encapsulation, a precipitate was formed by mixing an aqueous solution of the ODN and the excipient (equal weight amounts). The precipitate was recovered by centrifugation, washed with ethanol, recovered by centrifugation, washed with ethyl acetate, recovered by centrifugation, suspended in methylene chloride, and added to a solution of polymer (10% RG 502H in methylene chloride). The suspension was sonicated and atomized into liquid nitrogen following the process described in Example 1. The polymer solvent was extracted with ethanol, and the microparticles were recovered and dried. Release kinetics are shown in Table 2.

TABLE 2

| Excipient | w/w % ODN/ microparticle | w/w % added excipient | % ODN released at 1 hr.* | % ODN released at 24 hrs. | % ODN released at 3 days |
|---|---|---|---|---|---|
| Spermine | 5** | 0 | 0.9 ± 1.3 | 1.7 ± 1.3 | 2.4 ± 1.3 |
| Zinc Acetate | 5.1 ± 0.3 | 0 | 29.1 ± 0.3 | 33.4 ± 0.4 | 34.1 ± 0.2 |
| Zinc Acetate | 4.9 | 5% Zn carbonate | 52.5 ± 2.2 | 57.0 ± 2.0 | 58.0 ± 2.4 |

*in 2 mM Tris-Cl, pH 7.8
**theoretical rather than measured load

These results show that the amount of ODN released initially from the microparticles containing spermine or zinc complexed ODN was reduced substantially compared to that from the microparticles containing uncomplexed ODN (Table 1).

An additional experiment was done to investigate the effect of stabilized ODN load on the initial release. The antisense ODN described in Example 1 was complexed using zinc acetate and encapsulated as above, with load values of 1, 5, and 15%. The results are shown in Table 3.

TABLE 3

| Excipient | w/w % ODN/ microparticle* | % ODN released at 24 hours** |
|---|---|---|
| Zinc Acetate | 1 | 12.9 |
| Zinc Acetate | 5 | 15.1 |
| Zinc Acetate | 15 | 38.3 |

*theoretical load
**mean of two samples

These results show that the lower loads of ODN (1 and 5%) give comparable initial release values. However, increasing the load to 15%, increased the initial release over the 1% and 5% loads. However, the initial release of the 15% load was still significantly improved over that seen when stabilized ODN was encapsulated.

Complexation and encapsulation were repeated using a 15-mer c-myc phosphorothioate oligodeoxynucleotide having the sequence 5'-AACGTTGAGGGGCAT-3' (SEQ ID NO. 1), which is complementary to the translation initiation codon and downstream sequences of the human c-myc, and zinc acetate at an approximately 5% theoretical load. The load of the ODN in the microparticles was determined by dissolving the microparticles in 1N NaOH and measuring the amount of nucleotide by absorbance at $OD_{260}$. The mean particle diameter was measured using a Coulter counter.

TABLE 4

| Microparticle Lot | Oligonucleotide Load | Mean Diameter (by volume) |
|---|---|---|
| C | 4.32% | 89.6 microns |
| D | 4.17% | 86.9 microns |

Figure 2:
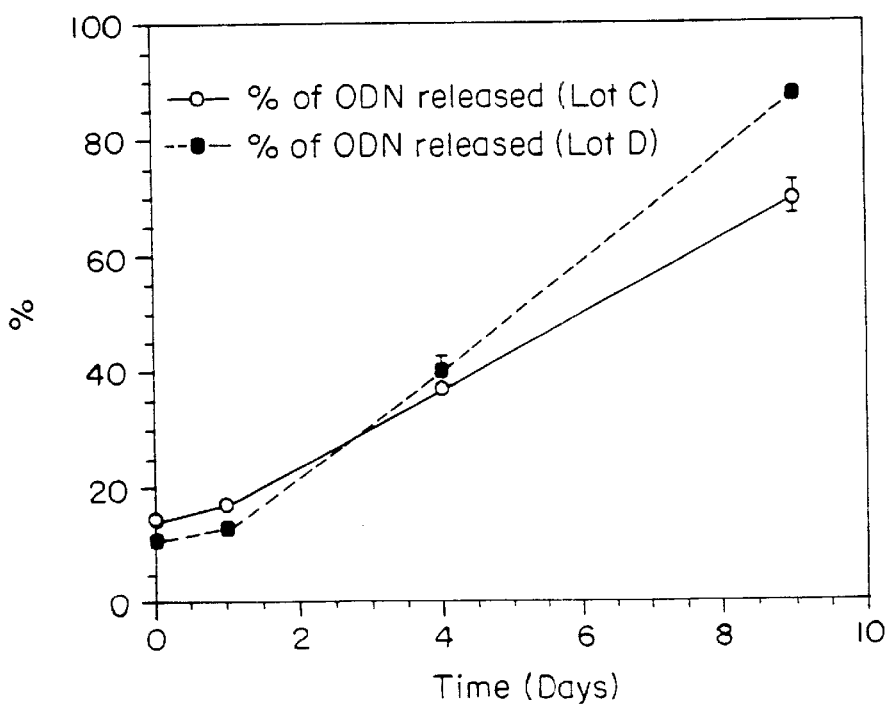
FIG. 2 is a plot of the % of antisense ODN released over time for microparticles containing a 5% theoretical load of antisense ODN having the sequence 5'-AACGTTGAGGGGCAT-3' (SEQ ID NO. 1), as described in Example 3.

The results of the in vitro release are shown in FIG. 2.

EXAMPLE 4

In Vivo Experiments

Oligodeoxynucleotide

The same 15 mer c-myc phosphorothioate oligodeoxynucleotide having the sequence 5'-AACGTTGAGGGGCAT-3' (SEQ ID NO. 1) was employed in the following in vivo studies.

To address the question of whether microencapsulation of ODNs might enhance the anti-leukemic effects of oncogene-targeted ODNs, we compared the effects of delivering an ODN as a daily bolus injection with delivery of the ODN encapsulated in microparticles.

Preparation of Microparticles Containing Stabilized ODN

To prepare the ODN for encapsulation, a precipitate was formed by mixing aqueous solutions containing equal weights of the ODN and zinc acetate. The precipitate was recovered by centrifugation (15K rpm, 10 minutes), washed with ethanol, recovered by centrifugation, washed with ethyl acetate, recovered by centrifugation, suspended in a solution of PLGA polymer (10% RG 502H in methylene chloride). The suspension was sonicated and atomized into liquid nitrogen using the process described in Example 1. The theoretical load of ODN in the final microparticle product was 5%. The load of the ODN in the microparticle was determined by dissolving the microparticle in 1N NaOH and measuring the amount of nucleotide by absorbance at $OD_{260}$.

A. Leukemia Model

Background

When injected into SCID mice, leukemic cells, especially those with a lymphatic phenotype, display primarily hematogenous spread, first invading the lymphohematopoietic system and then diffusing to other organs, closely reproducing the growth pattern and organ predilection seen in the actual clinical context. In particular, the BV173 Philadelphia cell line (human chronic myeloid leukemia) provides an excellent model because the survival of the mice carrying these cells is directly proportional to the leukemic cell load. Philadelphia[1] refers to a chromosome translocation of the proto-oncogene ABL from chromosome 9 to the breakpoint cluster region (BCR) on chromosome 22, resulting in the formation of BCR-ABL hybrid genes. The Philadelphia[1] chromosome translocation is the most common genetic abnormality in human leukemias.

The therapeutic potential of [S]ODNs has been assessed using SCID mice transplanted with human leukemic cells as a model system. Using SCID mice injected with $10^6$ BV173 cells and treating with BCR/ABL or c-myc antisense ODNs (daily injections of 1 mg/mouse/9 consecutive days, 1 or 3 weeks post-injection) it has been demonstrated by others that the disease process was temporarily suppressed, shown by a prolongation of the survival of antisense ODN-treated mice compared to controls. The anti-leukemia effects of the bcr-abl and c-myc ODNs in combination, using SCID mice bearing Philadelphia[1] cells (the BV173 line or primary cells from a patient with CML-blast crisis) has also been investigated. The rationale for using this was drawn from the knowledge that 1) myc expression is essential for cell proliferation, 2) there is a selective increase of c-myc expression in myeloid hematopoietic cell lines constitutively expressing v-abl; and 3) c-myc and v-abl synergize in vitro and in transgenic models of plasmacytomas. Studies with the BV173 line have shown that the ODN combination therapy had a greater therapeutic effect than each compound used individually. Ultimately, however, all animals succumbed to the disease process which could have been due to 1) a failure to reach sufficiently high ODNs concentration in each tissue so as to reduce the number of leukemic cells below the threshold required from manifestation of the leukemic process, or 2) the limited therapeutic potential of the [S]ODN derivatives, or 3) an intrinsic limitation in the choice of the targets of the ODNs therapy. (See Skorski et al., PNAS, 91:4504(1994) and Skorski et al., J. Exp. Med., 182:1645(1995).)

Treatment of BV173 Cells In Vivo with ODNs

SCID mice were intravenously injected with $10^6$ BV173 cells on day 0 to induce leukemia, then administered the first treatment 7 days later:

Group a Control: 5 mice untreated

Group b 10 mice treated with daily bolus i.v. injections of the 15-mer c-myc antisense solution described above (300 μg/mouse/day for 7 days)

Group c 10 mice treated with daily bolus subcutaneous injections of 15-mer c-myc antisense ODN described above solution (300 μg/mouse/day for 7 days)

Group d 10 mice treated with single subcutaneous bolus of 15-mer c-myc antisense ODN solution described above on day 1 (2.1 mg/mouse)

Group e 10 mice treated with single subcutaneous bolus of microparticles containing the 15-mer c-myc antisense ODN described above on day 1 (2.1 mg/mouse)

Mice were monitored for survival and leukemic burden in spleen and bone marrow, as described below.

Determination of Leukemic Burden

At 4 weeks post BV173 cell injections, disease progression was assessed by analyzing the presence of leukemic cells in spleen (SPL) and bone marrow (BMC) by clonogenic assay (leukemia-colony forming cells) and detection of bcr-abl transcripts by reverse transcriptase (RT-PCR).

Clonogenic Assay

Cells were obtained from the spleen (SPL) and bone marrow (BMC) of mice from each of the five treatment groups. $1 \times 10^5$ cells were plated in methylcellulose (in the absence of growth factors to favor the growth of leukemic clonogenic cells) for 10 days. The plates were then scanned with an inverted microscope, and the total number of colonies and clusters were counted. Two animals from treatment Groups b through e and one animal from treatment Group a were evaluated. The results of the assay were as follows:

TABLE 5

| Treatment Group | Colonies/$10^5$ Cells | |
| --- | --- | --- |
| | BMC | SPL |
| a | 75 | 21 |
| b | 35.5 | 11.5 |
| c | 61.5 | 18.5 |
| d | 81.5 | 21 |
| e | 16.5 | 5 |

The results indicate a decrease in leukemic colonies in the group treated with microencapsulated ODN (Group e).

RT-PCR

RT-PCR amplification of bcr-abl transcripts present in the total RNA isolated from spleen and bone marrow was performed, followed by Southern blot hybridization following the procedure described in Skorski et al., Blood, 88:1005–1012 (1996). Analysis of the hybridization demonstrated that there was a decrease in cmyc mRNA in the microparticle treated group (i.e., treatment Group e).

Survival

Figure 3:
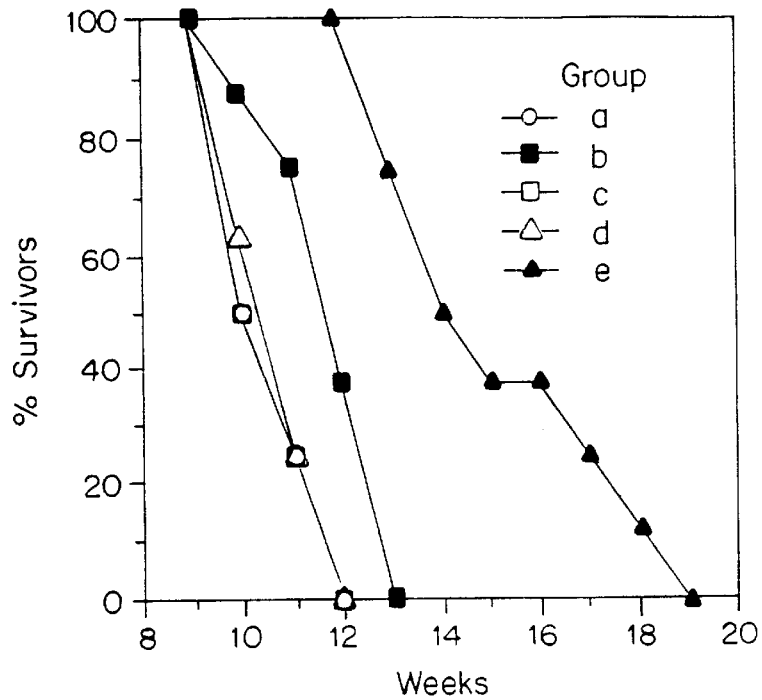
FIG. 3 is a plot of the percent of survivors for the Treatment Groups a–e versus time subjected to the leukemic animal model as detailed in Example 4.

Survival data for treatment Groups a–e is depicted graphically in FIG. 3. FIG. 3 shows that treatment Group e (microparticle treated) exhibited a significant increase in survival time as compared to the other treatment groups.

A further experiment using the leukemia model evaluated the effect of administering the microencapsulated ODN in cycles. SCID mice were intravenously injected with $10^6$ BV173 cells on day 0 to induce leukemia, then administered the first treatment 7 days later. Each of the treatment groups contained approximately 10 mice.

| Group | Treatment |
|---|---|
| Control | No ODN treatment |
| ODNs i.v. 7 days | Daily i.v. injections of ODN solution (0.3 mg ODN per day) for 7 days |
| sph + 1 | S.c. bolus of placebo microparticles administered on day 1 (amount of microparticles equivalent to Group d of the first experiment, 2.1 mg/mouse) |
| sph-ODNs + 1 | S.c. bolus of microparticles containing 2.1 mg ODN administered on day 1 |
| sph-ODNs + 1 + 15 | S.c. bolus of microparticles containing 1.05 mg ODN administered on each of days 1 and 15 |
| sph-ODNs + 1 + 15 + 29 | S.c. bolus of microparticles containing 0.7 mg ODN administered on each of days 1, 15, and 29. |

Figure 4:
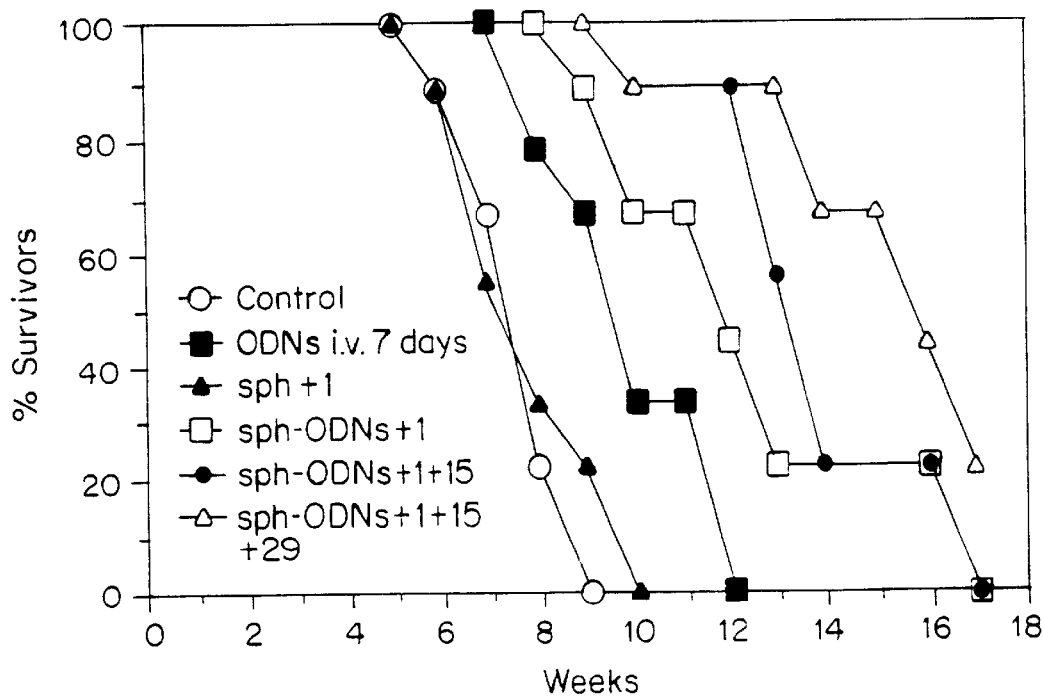
FIG. 4 is a plot of the percent of survivors for the control and treatment groups ODNs i.v. 7 days, sph+1, sph-ODNs+ 1, sph-ODNs+1+15, and sph-ODNs+1+15+29, subjected to the leukemic animal model as detailed in Example 4.

Survival data for the control and treated groups of this further experiment is depicted graphically in FIG. 4. FIG. 4 shows that for the treatment group sph-ODNs+1+15+29, 20% of the animals were alive at 17 weeks.

B. Melanoma Model

The effects of both intravenous (iv) and subcutaneous (sc) administration of the 15-mer c-myc phosphorothioate oligodeoxynucleotide having the sequence 5'-AACGTTGAGGGCCAT-3' (SEQ ID NO. 1), both encapsulated and unencapsulated, on human melanoma cells were assessed in vivo. The procedure followed for the in vivo experiment can be found in Leonetti et al., *Journal of the National Cancer Institute,* 88: No. 7, Apr. 3, 1996, the entire contents of which are hereby incorporated by reference.

The eight treatment groups assessed are described below. Each treatment group contained approximately 15 subjects.
Group 1: Control (no ODN treatment)
Group 2: 0.25 mg ODN solution i.v. daily for 8 days (total of 2 mg ODN/mouse)
Group 3: 0.25 mg ODN solution s.c. daily for 8 days (total of 2 mg ODN/mouse)
Group 4: 2 mg ODN encapsulated into microparticles s.c. at day 1 (total of 2 mg ODN/mouse)
Group 5: 1 mg ODN solution i.v. at days, 1, 3, 5, and 7 and 0.5 mg ODN solution i.v. at days 2, 4, 6, and 8 (total of 6 mg ODN/mouse)
Group 6: 1 mg ODN solution s.c. at days 1, 3, 5, and 7 and 0.5 mg ODN solution s.c. at days 2, 4, 6, and 8 (total of 6 mg ODN/mouse)
Group 7: 6 mg ODN encapsulated into microparticles s.c. at day 1 (total of 6 mg ODN/mouse)
Group 8: Equivalent amount of placebo microparticles as given in Group 7 on day 1.

The therapeutic efficacy of the treatment regimens was evaluated using the following end-points: 1) percent tumor weight inhibition (TWI), which was calculated by dividing mean tumor weight of the treated group by the mean of the control group, subtracting the resulting value from 1 and multiplying the value by 100. The tumor weight was calculated by caliper measurement according to the method described in Geran et al., *Cancer Chemother. Rep.,* 3: 1–88 (1972); and 2) % metastases reduction. The % metastases reduction was determined according to the procedure described in Leonetti et al., *JNCI* 88:419–429 (1996). Approximately 10 mice in each group were used to evaluate TWI (5 at each timepoint) and approximately 5 mice were used for the metastases analysis. Briefly, a predetermined number of animals from groups 1–8 were sacrificed at approximately 28 days after implantation. The lungs were removed and fixed to distinguish tumor nodules from lung tissue, and the number of metastases present was determined with the use of a dissecting microscope. The median number of metastases per treatment group was compared to the control group and the % reduction in metastases calculated. These results are shown in Table 6.

The results presented in Table 6 show that the microparticle treated groups (Groups 4 and 7) exhibit a significantly greater percent tumor weight reduction than the other treatment groups. In addition, percent metastases reduction is also significantly increased for the microparticle treated groups as compared to the other treatment groups.

TABLE 6

| Group | Treatment | TWI (%) Day 19 | TWI (%) Day 45 | Metastases Reduction (%) |
|---|---|---|---|---|
| Group 2 | 2 mg i.v. - 0.25 mg/day/8 day | 43 | 28 | 20 |
| Group 3 | 2 mg s.c. - 0.25 mg/day/8 day | 22 | 0 | 15 |
| Group 4 | 2 mg microparticles | 52 | 48 | 38 |
| Group 5 | 6 mg. iv. - 1 mg @ 1, 3, 5, 7 0.5 mg @ 2, 4, 6, 8 | 47 | 32 | 30 |
| Group 6 | 6 mg s.c. - 1 mg @ 1, 3, 5, 7 0.5 mg @ 2, 4, 6, 8 | 20 | 8 | 0 |
| Group 7 | 6 mg microparticles | 61 | 52 | 45 |

The results of Group 8 and Group 1 were similar.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A composition for the sustained release of an oligonucleotide from a polymer matrix, comprising:
   a) a biocompatible polymer; and
   b) a therapeutically effective amount of oligonucleotide which is complexed with a metal cation, wherein said oligonucleotide is dispersed within the biocompatible polymer.

2. The sustained release composition of claim 1 wherein the metal cation-complexed oligonucleotide is in the form of particles.

3. The sustained release composition of claim 1 wherein the biocompatible polymer is selected from the group consisting of poly(lactides), poly(glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, blends and copolymers thereof.

4. The sustained release composition of claim 3 wherein said polymer comprises poly(lactide-co-glycolide).

5. The sustained release composition of claim 1 wherein the metal cation of the metal cation-complexed oligonucleotide is multivalent.

6. The sustained release composition of claim 5 wherein the multivalent metal cation comprises a cation selected from the group consisting of: $Zn^{+2}$, $Ca^{-2}$, $Cu^{+2}$, $Mg^{+2}$ and any combination thereof.

7. The sustained release composition of claim 6 wherein the metal cation is $Zn^{+2}$.

8. The sustained release composition of claim 1 wherein the oligonucleotide is present from about 0.01% (w/w) to about 50% (w/w) based on the dry weight of the composition and the weight of the oligonucleotide prior to stabilization.

9. A method for providing a therapeutically effective amount of an oligonucleotide in a subject for a sustained period comprising administering to the subject a dose of the sustained release composition of claim 1.

10. A method for forming a composition for the sustained release of an oligonucleotide, comprising the steps of:
   a) dissolving a biocompatible polymer in a polymer solvent to form a polymer solution;
   b) adding a therapeutically effective amount of oligonucleotide which is complexed with a metal cation, to the polymer solution; and
   c) solidifying the polymer to form a polymer matrix containing a dispersion of said oligonucleotide.

11. The method of claim 10 wherein the biocompatible polymer is selected from the group consisting of poly(lactides), poly(glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, blends, and copolymers thereof.

12. The method of claim 11 wherein said polymer comprises poly(lactide-co-glycolide).

13. The method of claim 10 wherein the metal cation which is complexed to the oligonucleotide is a multivalent metal cation.

14. The method of claim 13 wherein the multivalent metal cation is selected from the group consisting of: $Zn^{+2}$, $Ca^{-2}$, $Cu^{+2}$, $Mg^{+2}$, and any combination thereof.

15. The method of claim 14 wherein the metal cation is $Zn^{+2}$.

* * * * *